(12) United States Patent
Moia et al.

(10) Patent No.: US 9,610,400 B2
(45) Date of Patent: Apr. 4, 2017

(54) DEVICE FOR MOVING A PISTON INSIDE A CARTRIDGE

(71) Applicant: Roche Diagnostics International AG, Rotkreuz (CH)

(72) Inventors: Franco Moia, Frenkendorf (CH); Marcel Mueller, Therwil (CH); Maurice Ducret, Burgdorf (CH)

(73) Assignee: ROCHE DIAGNOSTICS INTERNATIONAL AG, Rotkreuz (CH)

( * ) Notice: Subject to any disclaimer, the term of this patent is extended or adjusted under 35 U.S.C. 154(b) by 275 days.

(21) Appl. No.: 14/049,349

(22) Filed: Oct. 9, 2013

(65) Prior Publication Data
US 2014/0214000 A1    Jul. 31, 2014

Related U.S. Application Data

(63) Continuation of application No. PCT/EP2012/055354, filed on Mar. 26, 2012.

(30) Foreign Application Priority Data

Apr. 15, 2011 (EP) ..................................... 11003182

(51) Int. Cl.
A61M 5/142 (2006.01)
A61M 5/145 (2006.01)
(Continued)

(52) U.S. Cl.
CPC ...... *A61M 5/14216* (2013.01); *A61M 5/1458* (2013.01); *A61M 5/14566* (2013.01);
(Continued)

(58) Field of Classification Search
CPC ............ A61M 5/14216; A61M 5/1458; A61M 5/1782; A61M 5/14566; A61M 5/31515;
(Continued)

(56) References Cited

U.S. PATENT DOCUMENTS 4,677,980 A * 7/1987 Reilly .................. A61M 5/007
128/DIG. 1
5,336,189 A    8/1994 Sealfon
(Continued)

FOREIGN PATENT DOCUMENTS

EP    0170009 A1    2/1986
EP    0337252 A1    10/1989
(Continued)

*Primary Examiner* — Laura Bouchelle
*Assistant Examiner* — Justin L Zamory
(74) *Attorney, Agent, or Firm* — Woodard Emhardt Moriarty McNett and Henry LLP

(57) ABSTRACT

A device for moving a piston inside a cartridge having a cartridge body and the piston displaceable along a longitudinal axis of the cartridge body is presented. The device comprises a first portion having first coupler for coupling the cartridge body to the first portion such that in both directions of the longitudinal axis, a connection exists between the cartridge body and the first portion; and a second portion having second coupler for coupling the piston to the second portion such that in both directions of the longitudinal axis, a connection exists between the piston and the second portion. The first and second portions move relative to each other to effect at least a forward displacement of the piston coupled to the second portion inside the cartridge body coupled to the first portion along the longitudinal axis. The second coupler establishes and releases the connection with the piston.

12 Claims, 8 Drawing Sheets

(51) Int. Cl.
  *A61M 5/178* (2006.01)
  *A61M 5/315* (2006.01)
  *B23P 15/10* (2006.01)
  *A61J 1/06* (2006.01)

(52) U.S. Cl.
  CPC ...... *A61M 5/1782* (2013.01); *A61M 5/31515* (2013.01); *B23P 15/10* (2013.01); *A61J 1/062* (2013.01); *Y10T 29/49252* (2015.01)

(58) Field of Classification Search
  CPC .......... A61M 5/31586; A61M 5/31511; A61M 2005/14533; B25J 9/105; B25J 9/126; B25J 15/0028; B25J 15/0226; B25J 1/02; B25J 1/04; A61F 2/588
  See application file for complete search history.

(56) References Cited

U.S. PATENT DOCUMENTS

| | | | |
|---|---|---|---|
| 5,865,804 A * | 2/1999 | Bachynsky | A61M 5/2033 604/131 |
| 7,798,377 B2 | 9/2010 | Imhof et al. | |
| 2003/0038492 A1 * | 2/2003 | Kruger | B25J 15/0226 294/197 |
| 2006/0151545 A1 | 7/2006 | Imhof et al. | |

FOREIGN PATENT DOCUMENTS

| | | |
|---|---|---|
| EP | 1484071 A1 | 12/2004 |
| EP | 1779830 A1 | 5/2007 |
| FR | 2091684 A5 | 1/1972 |
| WO | 2005/002652 A2 | 1/2005 |

* cited by examiner

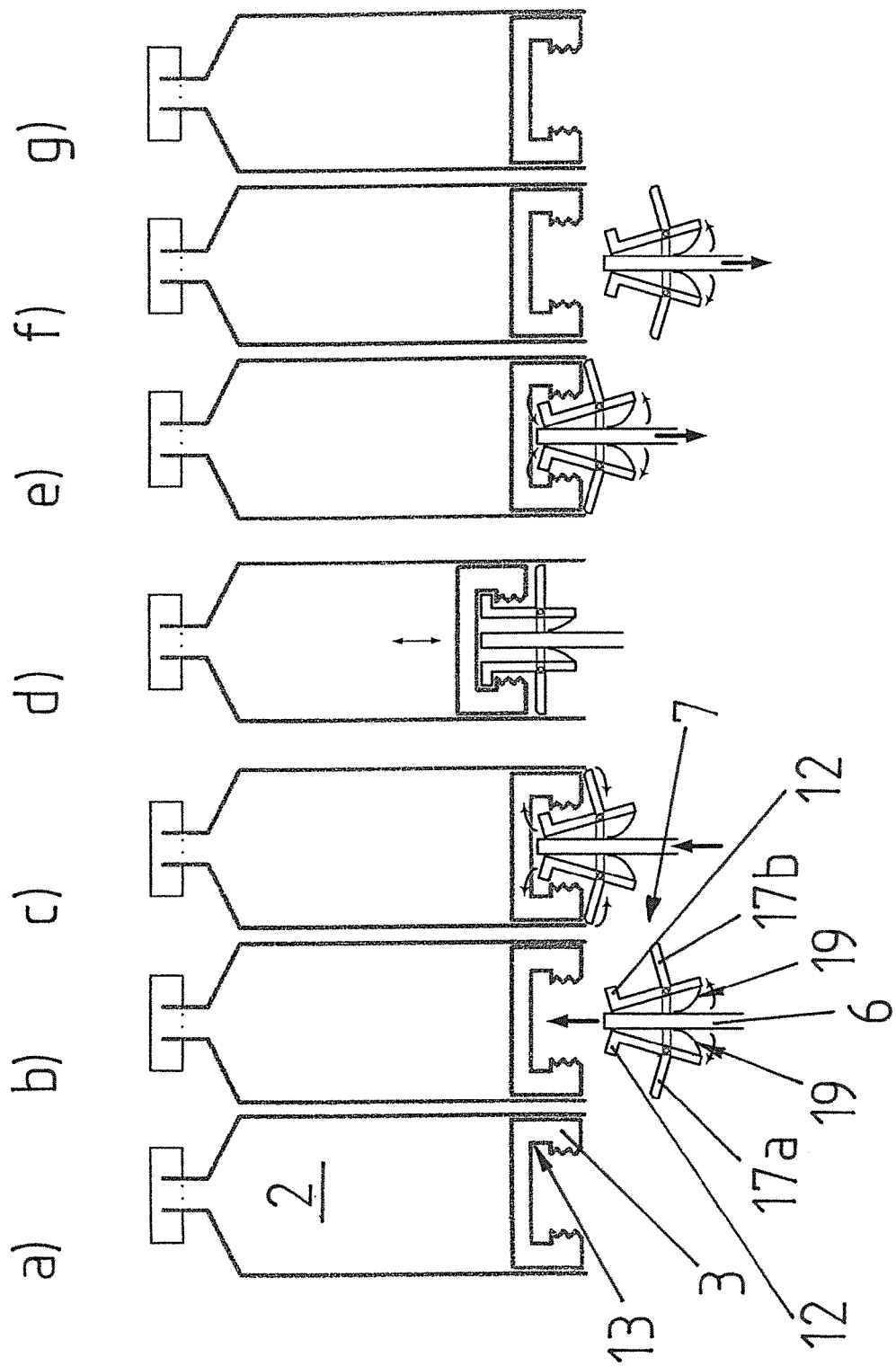

DEVICE FOR MOVING A PISTON INSIDE A CARTRIDGE

CROSS-REFERENCE TO RELATED APPLICATIONS

This application is a continuation of PCT/EP2012/055354, filed Mar. 26, 2012, which is based on and claims priority to EP 11003182.0, filed Apr. 15, 2011, which is hereby incorporated by reference.

BACKGROUND

The present disclosure generally relates to liquid-filled cartridges and, in particular, to a liquid-filled cartridge having a piston wherein the piston moves inside a cartridge, to a system comprising the device as well as to a method using the cartridge.

A typical problem when dispensing or dosing a liquid from a cartridge, e.g. when dosing insulin from an insulin cartridge with an automated insulin pump, is not only to make sure that, for dispensing the liquid, the piston can be pushed forward inside the cartridge body in a controlled manner, but also that the piston cannot be sucked into the cartridge body by a pressure differential between the front and back side of the piston.

Furthermore, when filling the cartridge with a liquid from a liquid reservoir by retracting the piston inside the cartridge body, a further problem is to make sure that, even though a maximum stroke of the piston can be utilized, there is no risk that the piston will be drawn out of the cylinder body.

From the prior art, different approaches to solve these problems are known. For dispensing or dosing liquid from a cartridge or for filling a cartridge with a liquid by an automated device, it is known to fix the cartridge body inside the device and to connect the piston with a threaded connection to a piston rod of the device by which it can be pushed forward and/or be retracted in a controlled manner inside the cartridge body within the limits of its design stroke.

For manually filling cartridges or syringe assemblies, it is furthermore known to provide a physical stop for the piston at the end of the cartridge body or of the cylinder of the syringe assembly to prevent the piston from being drawn out of the cartridge body or syringe cylinder.

Furthermore, cartridges or syringe assemblies are known having a piston which provides, on its backside, moveable couplings which, in a positive manner, engage an especially adapted piston rod once this piston rod is pushed towards the backside of the piston and, once coupled to the piston rod, release the piston rod only in case they are retracted by the piston rod past a defined position within the cartridge body or syringe cylinder.

Furthermore, a cartridge is known having a piston which provides, on its backside, a threaded pin for coupling it to a piston rod. This threaded pin is formed by an element which is disconnected from the piston once the piston is retracted into a defined position within the cartridge body by a piston rod threaded onto the threaded pin.

However, the known solutions using a threaded connection for coupling the piston to a piston rod suffer from the disadvantage that they require a complex relative motion between the piston and the piston rod for establishing and releasing the connection, which is undesirable since it requires certain skills of the user or, in case of an automated device, a complex mechanical arrangement for controlling the motion of the piston rod. Also, there is the disadvantage that the quality of the connection to be established and the possibility to release it later on is influenced by the friction between the piston and the cartridge body or the syringe cylinder, since this friction defines the torque which can be applied to the threaded connection.

The solutions providing a physical stop for the piston at the end of the cartridge body or of the cylinder of the syringe assembly have the disadvantage that in the manufacturing of the cartridge or syringe assembly, additional operating steps are required, which increases the manufacturing costs.

The solutions providing moveable couplings at the backside of the piston which release the piston rod once the piston is retracted into a defined position or providing an element for connection with the piston rod which element is disconnected from the piston once the piston is retracted into a defined position have the disadvantage that the piston is of complex design and as a result is difficult to manufacture and expensive.

Additionally, all of the know solutions suffer from the disadvantage that they require relatively expensive cartridge or syringe assembly designs that reduce the attractiveness to use them in fields where the cartridge or syringe assembly should be an inexpensive single use article, like, for example, a self-filled insulin cartridge for the therapy of diabetes.

Therefore, there is a general need for improvements in this area.

SUMMARY

According to the present disclosure, a device, system and method for moving a piston inside a cartridge having a cartridge body and a piston arranged therein displaceable along a longitudinal axis (Z) of the cartridge body is presented. The device can comprise a first portion having first coupler for releasably coupling the cartridge body of the cartridge to the first portion in such a manner that in both directions of the longitudinal axis (Z) of the cartridge body, a positive and/or frictional connection between the cartridge body and the first portion can exist and a second portion having second coupler for releasably coupling the piston of the cartridge to the second portion in such a manner that in both directions of the longitudinal axis (Z) of the cartridge body, a positive and/or frictional connection between the piston and the second portion can exist. The first and second portions can move relative to each other in order to effect at least a forward displacement of the piston coupled to the second portion inside the cartridge body coupled to the first portion along the longitudinal axis (Z) of the cartridge body. The second coupler can establish and release the positive and/or frictional connection with the piston and its shape can be reversibly changed.

Accordingly, it is a feature of the embodiments of the present disclosure to improve the filling, dosing and dispensing of cartridges with liquid. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 8 illustrates a schematic illustration of different steps a) to g) of an alternative coupling concept according to an embodiment of the present disclosure.

DETAILED DESCRIPTION

Figure 1:
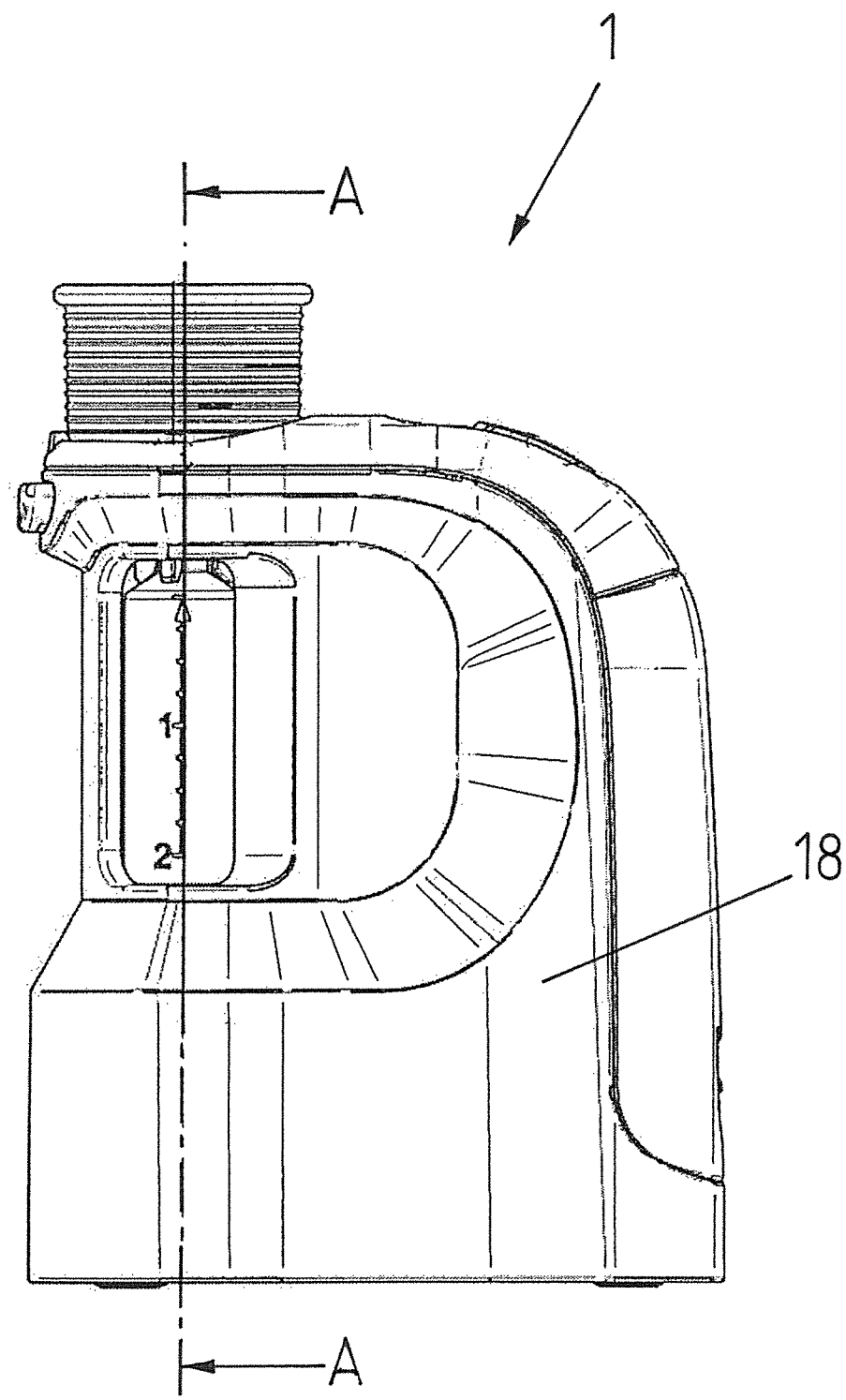
FIG. 1 illustrates a side view of a device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A device for moving the piston inside a cartridge having a cartridge body and a piston displaceable along a longitudinal axis of the cartridge body is disclosed. Such cartridges generally can be liquid tight containers comprising a container body with a cylindrical interior space defining a longitudinal axis and with a piston arranged in the interior space, which in a liquid tight manner can abut to the boundary walls of the interior space and can move within the interior space along the longitudinal axis in order to increase or reduce the volume of the fluid tight space defined by the boundary walls of the interior space and by the front face of the piston.

Such a device for moving the piston inside a cartridge having a cartridge body and a piston displaceable along a longitudinal axis of the cartridge body can comprise a first portion having first coupler for releasably coupling the cartridge body of the cartridge to the first portion in such a manner that in both directions of the longitudinal axis of the cartridge body, a positive and/or frictional connection between the cartridge body and the first portion can exist; and a second portion having second coupler for releasably coupling the piston of the cartridge to the second portion in such a manner that in both directions of the longitudinal axis of the cartridge body, a positive and/or frictional connection between the piston and the second portion can exist. The first and second portions can move relative to each other in order to effect, at least a forward displacement of the piston coupled to the second portion inside the cartridge body coupled to the first portion along the longitudinal axis of the cartridge body. The second coupler can establish and release the positive and/or frictional connection with the piston and can reversibly change its shape.

The connections established with the first and second couplers between the first portion and the cartridge body and between the piston and the second portion in each case can be greater than the frictional forces between the piston and the boundary walls of the cartridge body when moving the piston inside the cartridge and then the forces generated in the filling and/or dispensing operation of the cartridge by pressure differentials established between the front and back side of the piston. The first portion and the second portion can move relative to each other in such a manner that when the cartridge body of a cartridge is coupled via the first coupler to the first portion and the piston of the cartridge is coupled via the second coupler to the second portion, at least a forward displacement of the piston along the longitudinal axis of the cartridge body can be effected by their relative movement. The second coupler can establish and release the positive and/or frictional connection with the piston and can reversibly change its shape.

By this design, it can become possible to generate a system comprising this device and a cartridge releasably coupled to the first and second couplers of the device, wherein the cartridge can be of a simple, inexpensive design, thus making the system attractive for use in fields where the cartridge may need to be an inexpensive single use article, like, for example, for use as a system for filling self-filled insulin cartridges for the therapy of diabetes or as a system for dosing or dispensing insulin from a single use cartridge.

In one embodiment of such a device suitable for use in filling the cartridge with a liquid, for example, with a liquid drug such as insulin, the first and second portions of the device can move relative to each other in such a manner that for filling the cartridge with a liquid, they can effect a forward and a backward displacement of the piston coupled to the second portion along the longitudinal axis of the cartridge body inside the cartridge body coupled to the first portion.

Such a device can comprise a first portion having first coupler for releasably coupling the cartridge body of the cartridge to be filled to the first portion in such a manner that in both directions of the longitudinal axis of the cartridge body, a positive and/or frictional connection between the cartridge body and the first portion can exist; and a second portion having second coupler for releasably coupling the piston of the cartridge to be filled to the second portion in such a manner that in both directions of the longitudinal axis of the cartridge body, a positive connection and/or a frictional connection between the piston and the second portion can exist. The first and second portions can move relative to each other in order to effect, a forward and backward displacement of the piston coupled to the second portion inside the cartridge body coupled to the first portion along the longitudinal axis of the cartridge body. The second coupler can establish and release the positive and/or frictional connection with the piston and can reversibly change its shape.

Advantageously, the device can have a drive for moving the first and second portions relative to each other, like, for example, a battery powered electric motor with a dedicated gear and linkage. Such devices can be automated and thus can allow convenient use without specialized skills.

In a further embodiment, the second coupler's change in shape can partially or solely be effected through a contact with the piston and/or with the cartridge body of the cartridge, e.g. through a contact force which can act on a linkage mechanism of the second coupler which, as a result, can change the shape of the second coupler or e.g. through an electrical contact switch which initiates a change in shape of the second coupler through an electrically driven mechanism. This coupling concept can have the advantage, that the connection between the piston and the second coupler can be established when they are brought into a specific position relative to each other and thus there may be no need to separately identify the position of the piston and the second portion for establishing the connection.

In still a further embodiment, the second coupler's change in shape can partially or solely be effected through a controller of the device, like for example, through an electrically driven linkage mechanism which in dependency of the position of the second portion relative to the first portion can change the shape of the second coupler. This concept can have the advantage, that the connection between the piston and the second coupler can be established independently of a prior contact between the piston or the cartridge body and the second coupler and thus without loading the piston or the cartridge body with any forces through the second coupler before establishing the connection.

Advantageously, the shape of the second coupler can be changed when the first and the second portions assume a specific position relative to each other. This functionality can make sure that the connection between the second portion of the device and the piston of the cartridge can be established and can be released in specific relative positions of the first and second portions relative to each other, for example, can be established and released in relative positions which correspond to a fully retracted position of the piston of the cartridge received in the device for filling, which can be useful for filling cartridges, or for example, can be established in a relative position which can correspond to a fully retracted position of the piston of the cartridge received in the device for dispensing liquid from it and can be released in a relative position which can correspond to a fully forwards pushed position of the piston of the cartridge, which can be useful for dispensing a liquid from a cartridge.

In another embodiment, the shape of the second coupler can automatically be changed when the first and the second portions are moved into a specific position relative to each other and/or are moved out of a specific position relative to each other. This can offer the advantage that the device can have an uncomplicated control concept and can be easy to understand and operate even for unskilled person.

In order to make sure that a release of the first coupler and a subsequent removal of the cartridge body from the first portion cannot result in the piston being pulled out of the cartridge body, it can be advantageous that shape of the second coupler can be changed into a coupled or engaging status when the cartridge body of a cartridge has been coupled to the first portion by the first coupler and/or that the shape of the second coupler is automatically changed into a released status when, after the cartridge body of a cartridge has been coupled to the first portion by the first coupler, the first coupler can be released.

In still a further embodiment, the second portion can move relative to the first portion forwards and backwards between a fully retracted position and a fully extended position along a longitudinal axis in order to effect, a forward and backward displacement of the piston inside the cartridge body. In this embodiment, the shape of the second coupler advantageously can automatically be changed when the second portion is moved into the fully retracted position and/or is moved out of the fully retracted position.

For example, the shape of the second coupler can automatically change from a releasing status into a coupling or engaging status when, starting from the fully retracted position, a forward movement of the second portion is initiated. The shape of the second coupler can also automatically be changed back to the releasing status when the second portion, after the forward movement, again reaches the fully retracted position. Such devices can be suitable as filling devices for self-filled cartridges.

In still a further embodiment, the second coupler can comprise a pincer having at least two pincer arms, the shape of which can be changed through a closing and opening movement of the pincer arms. The pincer arms can comprise protrusions extending away from them for engagement into radial undercuts formed in a piston of a cartridge to be filled. By such a pincer, the second coupler that can change its shape in order to establish and release a connection with a piston of a cartridge can in a reliable and cost effective manner be made available.

The pincer can be opened and closed by a controller of the device which, for doing so, can be brought into contact with contact surfaces of the pincer arms and can be moved relative to these contact surfaces in direction of the longitudinal axis of the cartridge body to open or to close the pincer. In this manner, the pincer can be actuated in a simple way and with a minimum of additional moveable parts.

The pincer can be guided in guides for linear movement and can be moved forwards and backwards by a cam wheel rotated by a drive.

The linkage between the cam wheel and the pincer can be realized in that the pincer can comprise a pin or key which can travel in a groove formed in the cam wheel. Thus, the pincer can be coupled with the cam wheel via a pin or key formed as the pincer travels in a groove formed in the cam wheel. Such a linkage for generating a movement of the second portion relative to the first portion can be simple in design, inexpensive in manufacturing and reliable in operation.

In an embodiment of such a device, the pincer can be opened and closed by a controller of the device which can be operated by the cam wheel. As a result, a forced mechanical coupling between the movement of the first and second portions relative to each other and the change in shape of the second couple can result.

In another embodiment, the controller for opening and closing the pincer can comprise a pusher which can be pushed up by a protrusion formed at the cam wheel, thereby pushing together the arms of the pincer. By this design, a simple and reliable mechanism for controlling the change in shape of the second coupler and the relative movement between the first and second portions of the device can result.

In the before mentioned embodiments in which both, the relative movement between the first and second portions as well as the opening and closing of the pincer can be controlled by a common cam wheel, it can be advantageous that the cam wheel be designed in such a manner that, while the pincer can be opened and closed by the controller operated by the cam wheel, the pincer which can be part of the second portion of the device can be held by the cam wheel in a fully retracted position. By this control concept, it can be possible to ensure that the pincer can be coupled to the piston of the cartridge in a defined position.

The cam wheel can be coupled to a drive unit, for example, an electrical motor with associated gear and control, via a rotationally flexible coupling. If the cam wheel is rotated forwards and backwards between two physical stops, control of the drive unit can be realized without the risk of overloading components due to recent torque peaks by monitoring the energy consumption of the drive unit and by stopping the drive unit or reverse its rotation direction once a specific energy consumption, for example, in the case of an electric motor, a certain electric current, can be detected. However, also other control concepts are envisaged, for example, sensors which can detect certain relative positions of the first and second portions or certain angles of rotation of the cam wheel.

In a further embodiment, the device can be a device for filling a cartridge with a liquid from a liquid reservoir or for dispensing or dosing a liquid from a cartridge containing a liquid, such as, for example, a liquid drug, such as, for example, insulin.

A system can comprise a device according to the disclosure and a cartridge having a cartridge body and a piston arranged therein displaceable along a longitudinal axis of the cartridge body. The cartridge body of the cartridge can be releasably coupled to the first coupler of the first portion of the device in such a manner that in both directions of the longitudinal axis of the cartridge body, a positive and/or frictional connection between the cartridge body and the first portion can exist. The piston of the cartridge can be releasably coupled to the second coupler of the second portion in such a manner that in both directions of the longitudinal axis of the cartridge body, a positive and/or frictional connection between the piston and the second portion can exist.

The connections which can be established between the first portion and the cartridge body and between the piston and the piston rod in each case can be greater than the frictional forces between the piston and the boundary walls of the cartridge body when moving the piston inside the cartridge and the forces generated in the intended use of the system, e.g. filling of the cartridge with a liquid and/or dispensing liquid from the cartridge, by pressure differentials between the front and back side of the piston.

Since the cartridge can be a simple, inexpensive design, the system can be attractive for use in fields where the cartridge should be an inexpensive single use article, like, for example, for use as a system for filling self-filled insulin cartridges for the therapy of diabetes or as a system for dosing or dispensing, respectively, insulin from a single use cartridge.

In one embodiment, the back side of the piston of the cartridge can comprise at least one radial undercut. The second coupler of the second portion of the device can comprise moveable parts, and, when the cartridge body is coupled by the first coupler to the first portion and the second portion is moved towards the piston and displaces the piston forwards inside the cartridge body, the moveable parts can be moved, such as, for example, against spring forces, at least partially through a contact with the piston and/or with the cartridge body, from a position, in which there is no engagement with the at least one radial undercut into a position in which they can engage the at least one radial undercut in such a manner that in both directions of the longitudinal axis of the cartridge body, a positive connection between the piston and the second portion can exist. When, during a subsequent backward displacement of the piston inside the cartridge body effected by the second portion, the piston can reach a specific retracted position within the cartridge body, the moveable parts can be moved, for example, by spring forces, from the position, in which they can engage the at least one radial undercut into the position in which there can be no engagement with the at least one radial undercut.

In another embodiment, the back side of the piston of the cartridge can comprises at least one radial undercut. The second coupler of the second portion can comprise moveable parts, and, when the cartridge body is coupled by the first coupler to the first portion, when the second portion is in the fully retracted position or in a specific almost fully retracted position and when a forward movement of the second portion can be initiated, the moveable parts, for example, by spring forces, at least partially controlled by a controller of the device, can be moved from a position, in which there is no engagement with the at least one radial undercut, into a position in which they can engage the at least one radial undercut in such a manner that in both directions of the longitudinal axis of the cartridge body, a positive connection between the piston and the second portion can exist.

This embodiment of a system can comprise a device, wherein the second coupler can be designed in such a manner that, when, after the forward movement of the second portion has been initiated, during a subsequent backward displacement of the piston inside the cartridge body effected by the second portion, the second portion can again reach the fully retracted position or the specific almost fully retracted position, the moveable parts can be moved, for example, against spring forces, at least partially controlled by a controller of the device, from the position, in which they can engage the at least one radial undercut into the position in which there is no engagement with the at least one radial undercut.

In another embodiment of the system, the back side of the piston of the cartridge can comprises at least one radial undercut, for engagement of the second coupler of the second portion of the device. The second coupler of the device can comprise moveable parts and, when the cartridge body is coupled by the first coupler to the first portion of the device and the second portion is moved towards the piston and starts to displace the piston forwards inside the cartridge body, the moveable parts of the second coupler can be moved, for example, against spring forces, partially or solely through a contact with the piston and/or with the cartridge body, from a position, in which there is no engagement with the at least one radial undercut in the piston into a position in which they can engage the at least one radial undercut in such a manner that in both directions of the longitudinal axis of the cartridge body, a positive connection between the piston and the second portion can exist enabling a forward and backward displacement of the piston through a movement of the second portion. Furthermore, the second coupler of the device can be designed in such a manner that when, during a subsequent backward displacement of the piston inside the cartridge body effected by the second portion the piston can reach a specific retracted position within the cartridge body, the moveable parts can be moved, for example, by spring forces, from the position, in which they can engage the at least one radial undercut back into the position in which there is no engagement with the at least one radial undercut.

As mentioned earlier, this coupling concept can have the advantage that the connection between the piston and the second coupler can be established when the piston and the second coupler can be brought into a specific position relative to each other and thus there can be no need to separately identify the exact positions of the piston and the second portion for establishing the connection.

In still a further embodiment of the system, again the back side of the piston of the cartridge can comprise at least one radial undercut, for engagement of the second coupler of the second portion of the device. The second coupler of the device can comprise moveable parts and can be designed in such a manner that, when the cartridge body is coupled by the first coupler to the first portion of the device and when the second portion of the device is in the fully retracted position or in a specific almost fully retracted position and when a forward movement of the second portion is initiated, the moveable parts of the second coupler, for example, by spring forces, partially or solely controlled by a controller of the device, can be moved from a position, in which there is no engagement with the at least one radial undercut in the piston, into a position in which they can engage the at least one radial undercut in such a manner that in both directions of the longitudinal axis of the cartridge body, a positive connection between the piston and the second portion can exist enabling a forward and backward displacement of the piston through a movement of the second portion.

As mentioned earlier, this coupling concept can have the advantage that the connection between the piston and the second coupler can be established independently of a prior contact between the piston and the second coupler and thus without any forces acting from the second portion onto the piston or the cartridge body before establishing the connection.

In this embodiment, the second coupler can be designed in such a manner that, when, after the forward movement of the second portion has been initiated, during a subsequent backward displacement of the piston inside the cartridge body can be effected through a movement of the second portion relative to the first portion, the second portion can again reach the fully retracted position or the specific almost fully retracted position, the moveable parts of the second coupler can be moved, for example, against spring forces, partially or solely controlled by a controller of the device, from the position, in which they can engage the at least one radial undercut in the piston back into the position in which there is no engagement with the at least one radial undercut. Such systems can be suitable as automated filling systems for self-filled cartridges.

The moveable parts of the device of the system can comprise or can be formed by the resilient arms of a pincer. Such a pincer can be reliable and inexpensive.

A method of moving the piston in a cartridge having a cartridge body and a piston arranged therein displaceable along a longitudinal axis of the cartridge body can comprise providing a system as discussed above. The cartridge body of the cartridge can be releasably coupled by the first coupler to the first portion of the device in such a manner that in both directions of the longitudinal axis of the cartridge body, a positive and/or frictional connection between the cartridge body and the first portion can exist. The piston of the cartridge can be releasably coupled by the second coupler to the second portion in such a manner that in both directions of the longitudinal axis of the cartridge body, a positive and/or frictional connection between the piston and the second portion can exist. The connection can be established through a change in shape of the second coupler. The piston can move inside the cartridge body along the longitudinal axis through a relative movement between the first and second portions of the device.

In one embodiment of the method, the method can fill a cartridge with a liquid, such as, for example, with a liquid drug, such as, for example, with insulin, from a liquid reservoir.

Since the cartridge can be of a simple, inexpensive design, the method can be attractive for use in fields where the cartridge may need be an inexpensive single use article, like for example, as method of filling self-filled insulin cartridges for the therapy of diabetes or as method of dosing or dispensing, respectively, insulin from a single use cartridge.

In one embodiment of such a method, the method can comprises providing a system and a liquid reservoir for filling a cartridge with a liquid from a liquid reservoir. The cartridge body of the cartridge can be releasably coupled by the first coupler to the first portion of the device in such a manner that in both directions of the longitudinal axis of the cartridge body, a positive and/or frictional connection between the cartridge body and the first portion can exist. The piston of the cartridge can be releasably coupled by the second coupler to the second portion in such a manner that in both directions of the longitudinal axis of the cartridge body, a positive and/or frictional connection between the piston and the second portion can exist. The connection can be established through a change in shape of the second coupler. The cartridge and the liquid reservoir can be connected in such a manner that the inside of the liquid reservoir and the inside of the cartridge can communicate with each other while they can hermetically be sealed against the outside. The volume of the inside of the cartridge can be increased by moving the piston through a relative movement between the first and second portions of the device backwards inside the cartridge body displacing liquid from the inside of the liquid reservoir into the inside of the cartridge.

In another embodiment, before the volume of the inside of the cartridge can be increased by moving the piston through a relative movement between the first and second portions of the device backwards inside the cartridge body for displacing liquid from the inside of the liquid reservoir into the inside of the cartridge, the volume of the inside of the cartridge can be reduced by moving the piston through a relative movement between the first and second portions of the device forwards inside the cartridge body.

In a further embodiment, the method can comprise providing a system with a cartridge containing a liquid to be dispensed or dosed. The cartridge body of the cartridge can be releasably coupled by the first coupler to the first portion of the device in such a manner that in both directions of the longitudinal axis of the cartridge body, a positive and/or frictional connection between the cartridge body and the first portion can exist. The piston of the cartridge can be releasably coupled by the second coupler to the second portion in such a manner that in both directions of the longitudinal axis of the cartridge body, a positive and/or frictional connection between the piston and the second portion can exist. The connection can be established through a change in shape of the second coupler. The piston can move forwards inside the cartridge body along the longitudinal axis through a relative movement between the first and second portions of the device dispensing liquid from the cartridge.

In another embodiment, a system can be provided comprising a device and a dedicated cartridge. Thereafter, the cartridge body of the cartridge and the piston of the cartridge can be releasably coupled by the first and the second couplers of the device to the first and second portions of the device in each case in such a manner that in both directions of the longitudinal axis of the cartridge body, there can exist a positive and/or frictional connection between the cartridge body and the first portion and between the piston and the second portion. For establishing the connection between the piston and the second portion, the shape of the second coupler can be changed. After the cartridge body and the piston of the cartridge have been coupled to the first and second portions of the device by the first and second couplers, the piston can be moved inside the cartridge body along the longitudinal axis of same through a relative movement between the first and second portions of the device.

In another embodiment, the cartridge, which can be coupled with its cartridge body and its piston to the first and second portions of the device by the first and second couplers, can be connected with a liquid reservoir containing a liquid in such a manner that the inside of the liquid reservoir and the inside of the cartridge can communicate with each other while they can be hermetically sealed against the outside. After the cartridge has been connected to the liquid reservoir, the piston can be moved inside the cartridge body along the longitudinal axis of same through a relative movement between the first and second portions of the device in such a manner that the volume of the inside of the cartridge can be increased displacing liquid from the inside of the liquid reservoir into the inside of the cartridge.

Before increasing the volume of the inside of the cartridge as described above for displacing liquid from the inside of the liquid reservoir into the inside of the cartridge, the piston can be moved inside the cartridge body along the longitudinal axis of same through a relative movement between the first and second portions of the device in such a manner that the volume of the inside of the cartridge is reduced. This can take place according to alternative embodiments of the method before or after the cartridge has been connected to the liquid reservoir.

In another embodiment, the method can dispense or dose a liquid, such as, for example, a liquid drug, such as, for example, insulin, from a cartridge containing the liquid. In this embodiment, the cartridge of the system which can be provided contains the liquid to be dosed or dispensed. After the cartridge body and the piston of the cartridge have been coupled to the first and second portions of the device by the first and second couplers, the piston can be moved inside the cartridge body along the longitudinal axis of same through a relative movement between the first and second portions of the device in such a manner that the volume of the inside of the cartridge can be reduced, thereby dispensing liquid from the cartridge.

Figure 2:
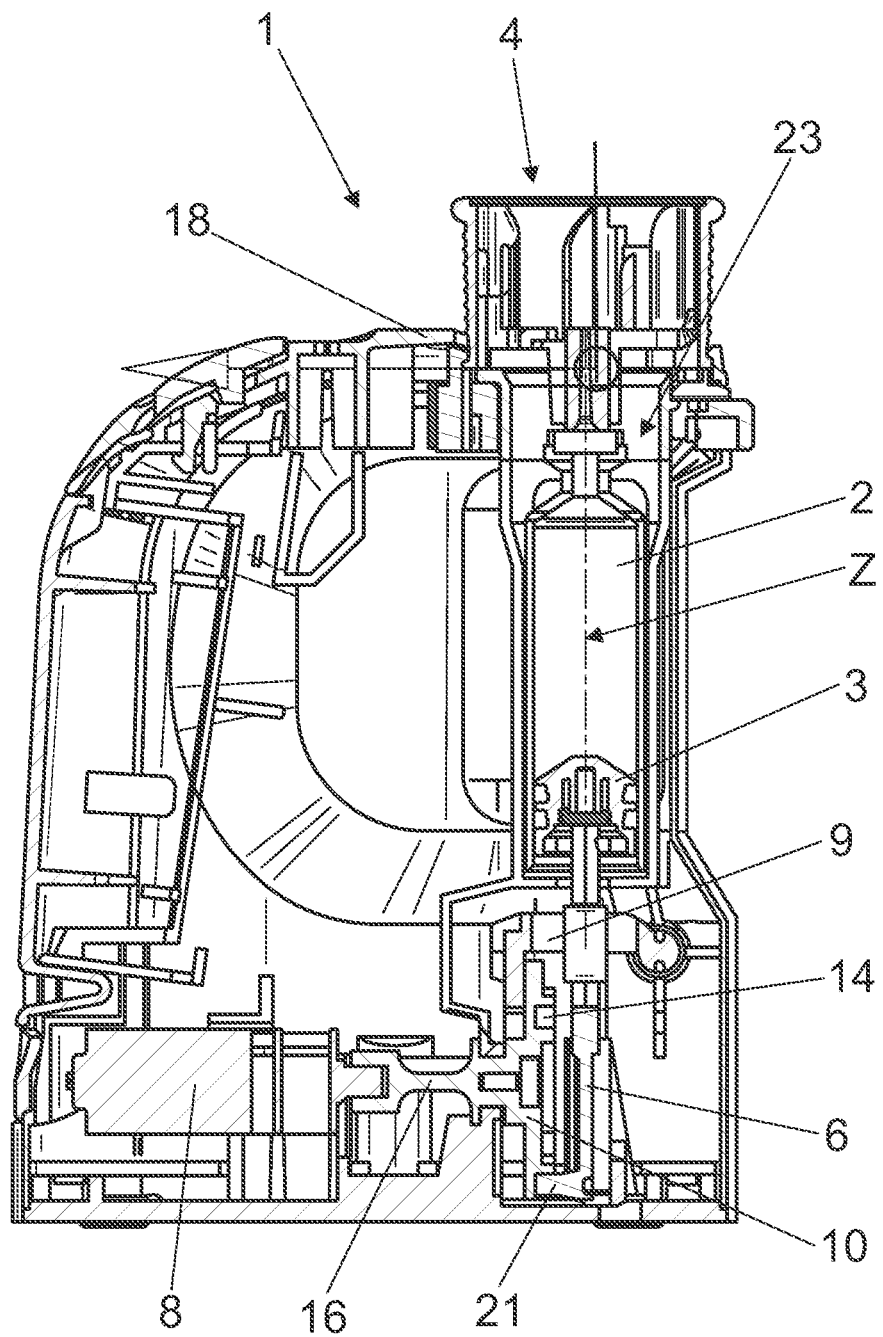
FIG. 2 illustrates sectional view of the device of FIG. 1 along line B-B in FIG. 3 according to an embodiment of the present disclosure.
Figure 3:
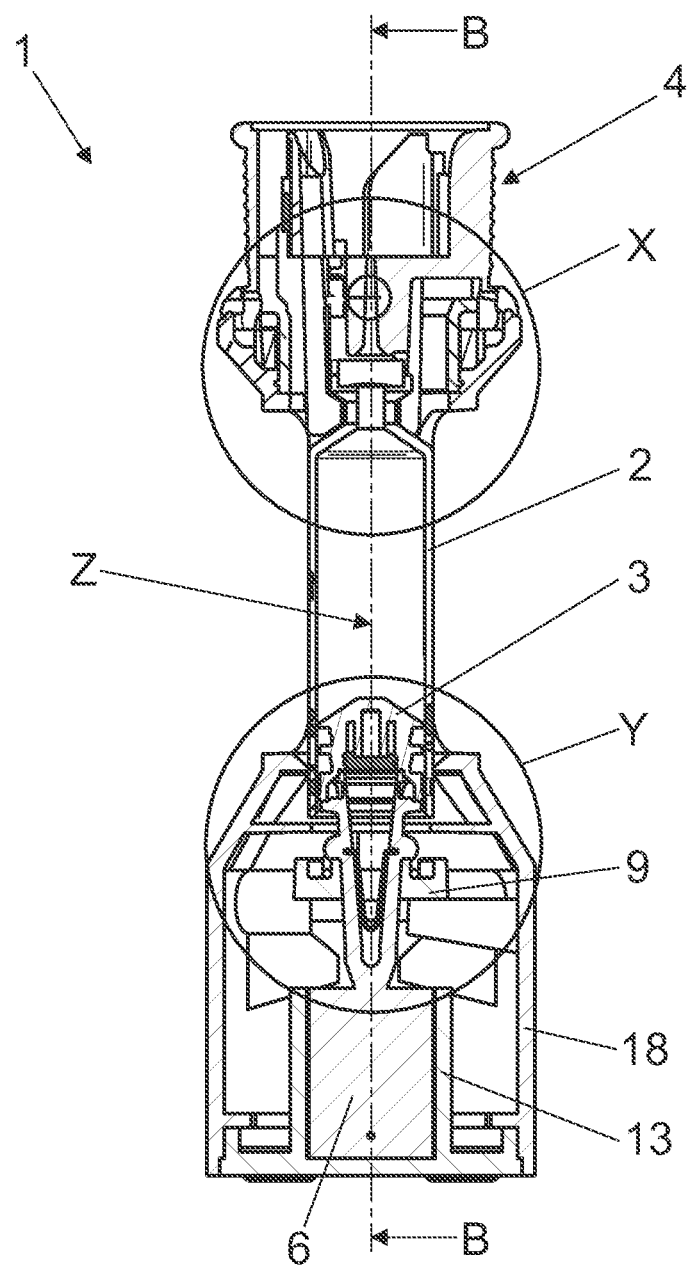
FIG. 3 illustrates a sectional view of the device of FIG. 1 along line A-A in FIG. 1 according to an embodiment of the present disclosure.

FIG. 1 shows a side view of a device 1 for filling self-filled insulin cartridges with insulin from an insulin reservoir. FIGS. 2 and 3 show sectional views of the device 1, once in section along the line A-A in FIG. 1 (FIG. 3) and once in section along the line B-B in FIG. 3 (FIG. 2), with a suitable cartridge 2, 3 received within the device 1. Thus, FIGS. 2 and 3 also show sectional views of a system with the device 1 of FIG. 1 and a suitable cartridge installed therein.

Figure 4:
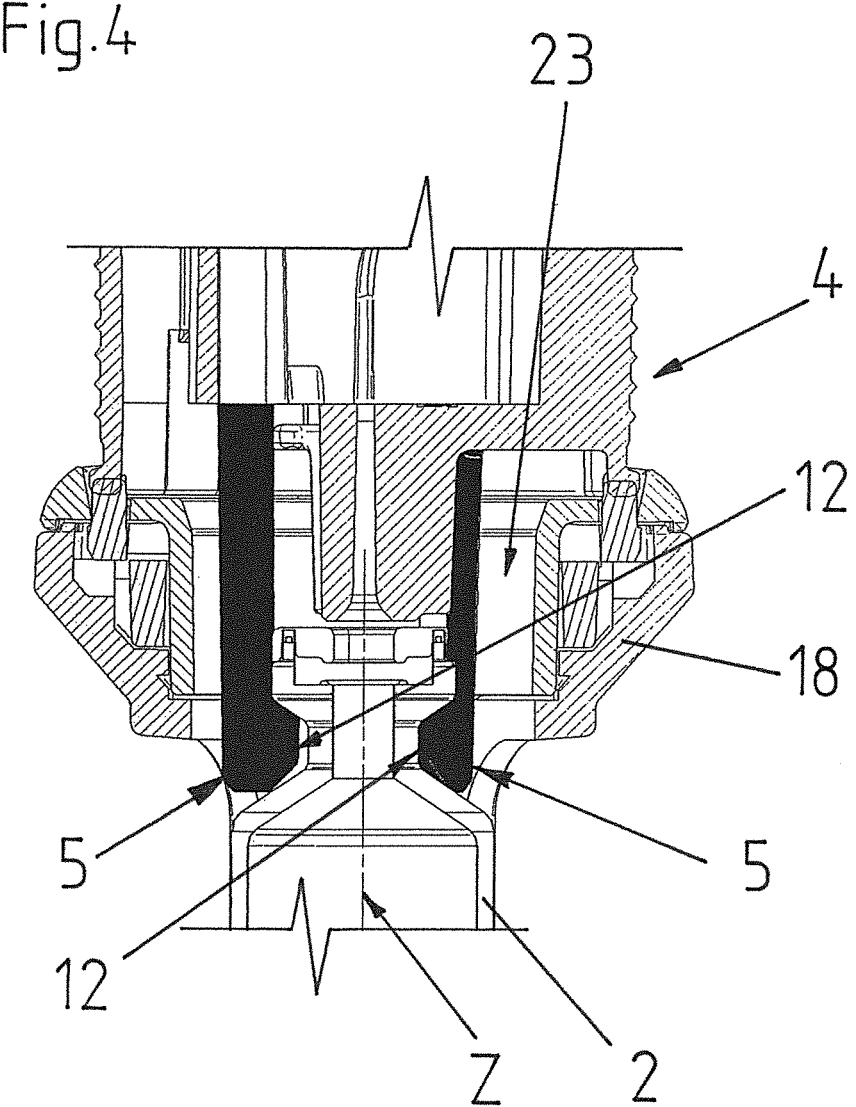
FIG. 4 illustrates the detail X of FIG. 3 according to an embodiment of the present disclosure.

As can be seen when in addition to the FIGS. 1 to 3 considering FIG. 4, which shows the detail X of FIG. 3, the cartridge body 2 of the cartridge can be releasably held inside the device 1 and can be connected to the housing 18 of the device 1 by a connector assembly 4, i.e., a first portion of the device. The connection with the connector assembly 4 can be established by arms 5, i.e., the first coupler, of the connector assembly 4 which can engage with protrusions 12 arranged at their free ends the radial undercut formed by the neck portion of the cartridge body 2 in such a manner that, in both directions of the longitudinal axis Z of the cartridge body 2, there can exist a positive connection between the cartridge body 2 and the connector assembly 4 and thus between the cartridge body 2 and the housing 18 of the device 1.

Figure 5:
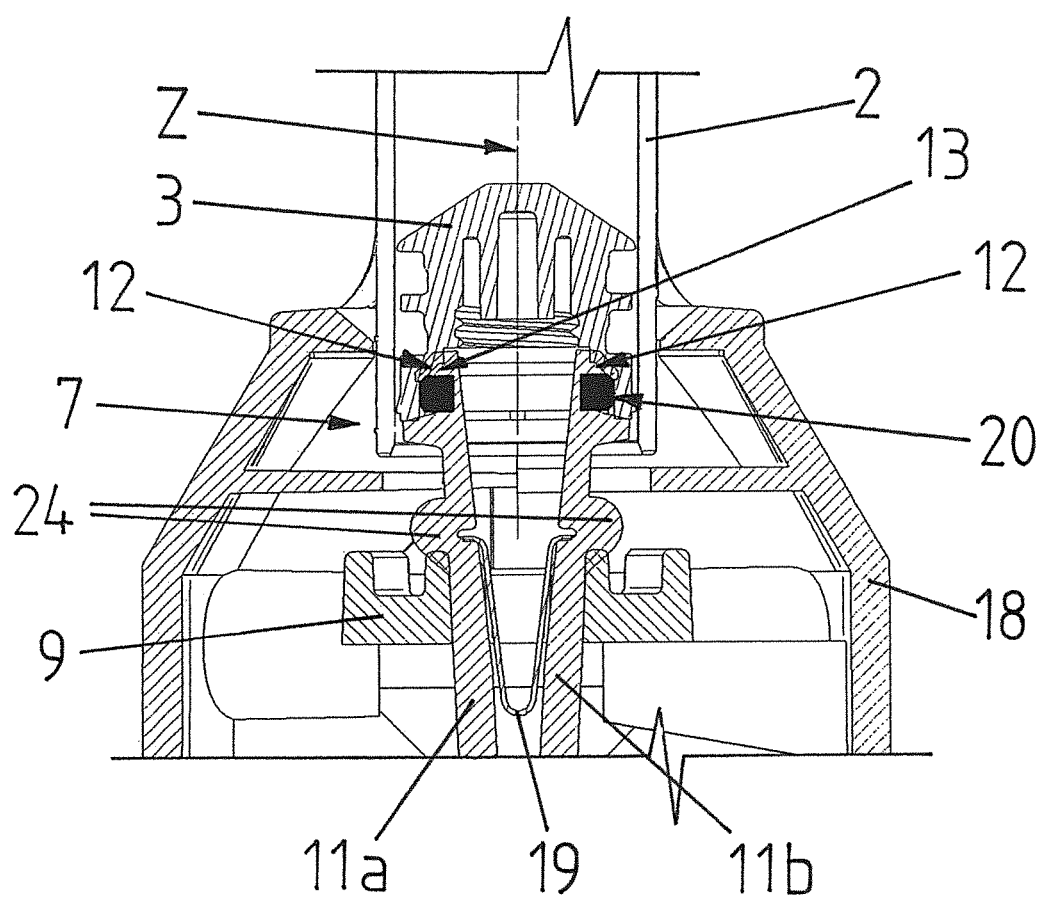
FIG. 5 illustrates the detail Y of FIG. 3 according to an embodiment of the present disclosure.

As can be seen in FIG. 5, which shows the detail Y of FIG. 3, the piston 3 of the cartridge can be releasably coupled at its backside to a pincer 7, i.e., the second coupler, having two resilient pincer arms 11a, 11b which can be spread by a spring 19. The pincer arms 11a, 11b can engage with protrusions 12 formed at their free ends a radial undercut formed by a ring 20 fixedly mounted in a central opening in the backside of the piston 3 in such a manner that in both directions of the longitudinal axis Z of the cartridge body 2, there can exist a positive connection between the piston 3 and the pincer 7.

Figure 6:
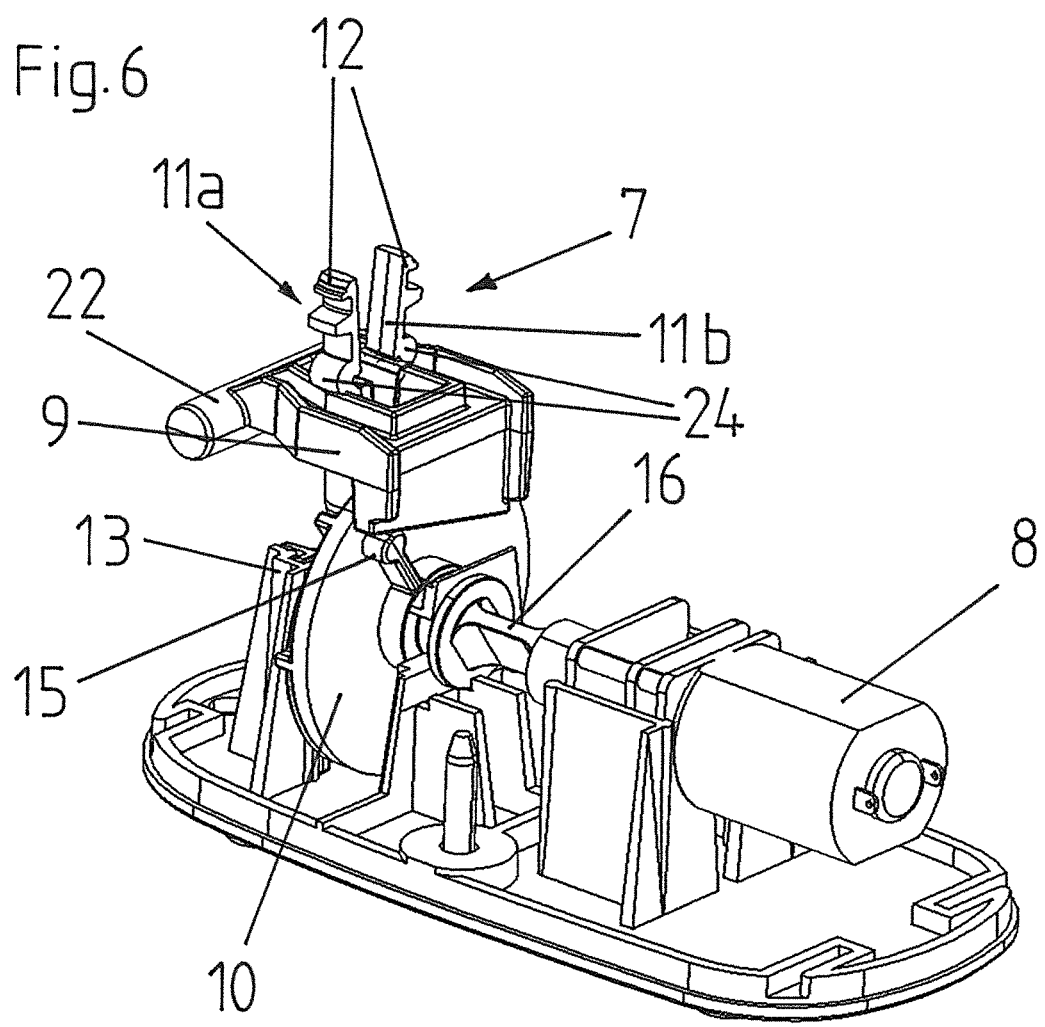
FIG. 6 illustrates shows a perspective view from a first direction onto the base plate of the device according to FIG. 1 with the pincer mechanism and the associated drive and control mechanism according to an embodiment of the present disclosure.
Figure 7:
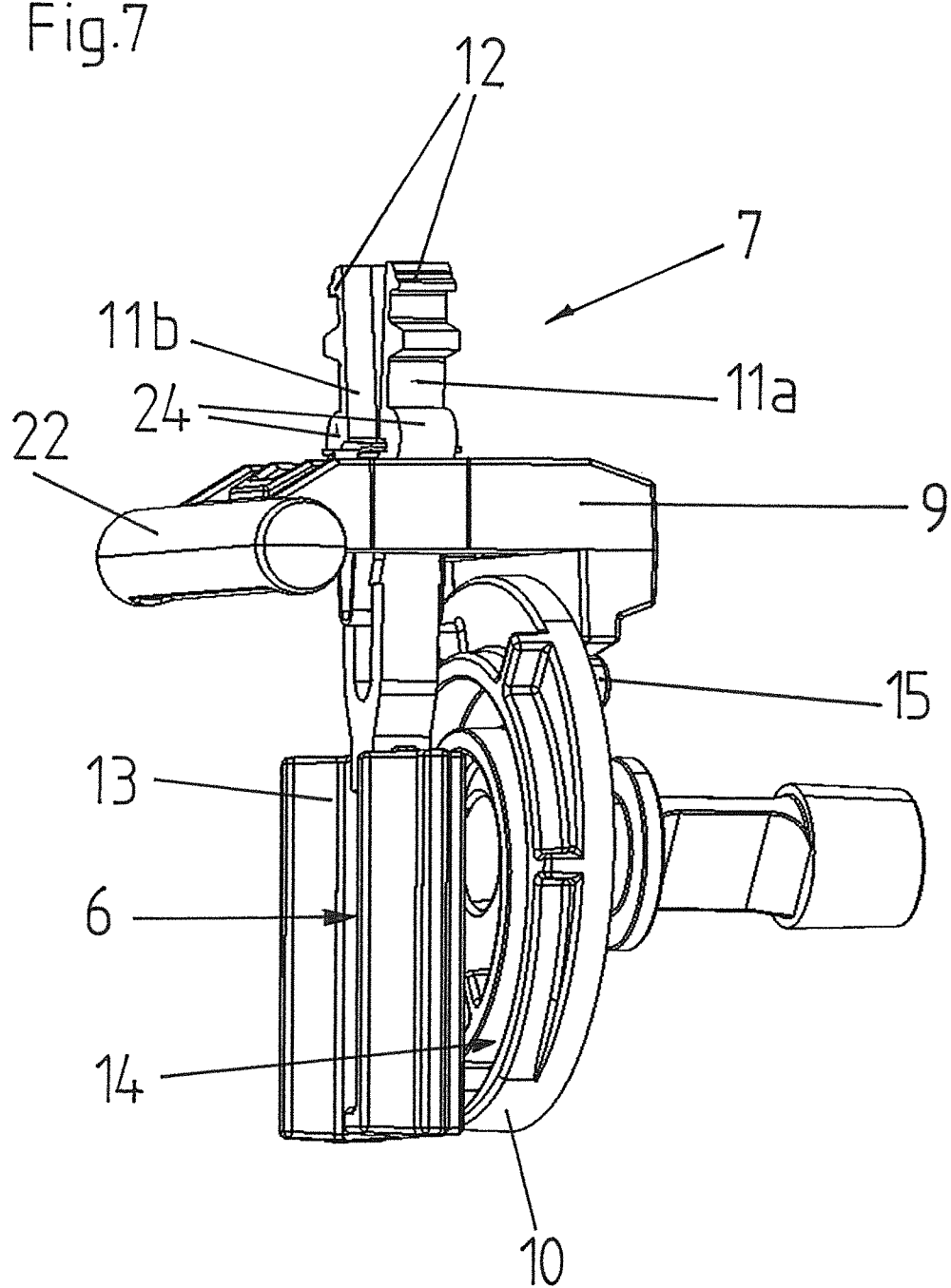
FIG. 7 illustrates a perspective view from a second direction onto the pincer mechanism and the associated control mechanism shown in FIG. 6 according to an embodiment of the present disclosure.

As can be seen in FIGS. 6 and 7, which show perspective views from different directions onto the pincer 7 and the associated drive, the pincer 7 can be part of a slider assembly 6, i.e., second portion, which can be guided in guides 13 for linear movement and can be moved forwards and backwards in direction of the longitudinal axis Z of the cartridge body 2 by a cam wheel 10 which can be rotated by an electric motor 8 coupled to it via an rotationally flexible coupling 16.

The linkage between the slider assembly 6 and the cam wheel 10 can be established by a pin 21 formed at the slider 6, which pin 21 can be received in a groove 14 formed in the cam wheel 10.

When rotating the cam wheel 10 with the motor 8 clockwise and anti-clockwise, the pin 21 can travel in the groove 14 between the two ends of the groove 14, thereby lifting and lowering the slider assembly 6 with its pincer 7 and, as a result, moving the piston 3 forwards and backwards in direction of the axis Z inside the cartridge body 2.

As can be seen, the two pincer arms 11a, 11b of the pincer 7 can extend through the opening of a rocker frame 9 which, by rotating the cam wheel 10 with the motor 8 clockwise and anti-clockwise within a certain angle of rotation, can at one end thereof be lifted and lowered by a protrusion 15 formed at the cam wheel 10, thereby tilting the rocker frame 9 around a bearing pin 22 located at its other end. Since the pincer arms 11a, 11b on the outside can comprise protrusions 24 which under resilient pre-stress contact sliding surfaces formed at the inside of the opening of the rocker frame 9, the tilting of the rocker frame 9 around its bearing pin 22 can result in an opening and closing movement of the arms 11a, 11b of pincer 7 relative to each other. Through this opening and closing of the pincer 7, the connection between the piston 3 and the slider assembly 6 can be established (the opening of the pincer) and be released (the closing of the pincer).

The cam wheel 10 with its groove 14 and the protrusion 15 can have the range of rotation in which its protrusion 15 can be lifting and lowering the end of the rocker frame 9 and thus the pincer 7 can be opened and closed, the slider assembly 6 with its pincer 7 can be held by its pin 21 which can be travelling in the groove 14 of the cam wheel 10 in a fully retracted position.

For loading a cartridge to be filled with insulin from an insulin reservoir into the device 1 and thus arrive at the situation shown in the FIGS. 2 and 3, in which the cartridge body 2 is connected via the arms 5 to the connector assembly 4 and to the housing 18 and in which the cartridge piston 3 can be connected via the pincer 7 to the slider assembly 6, the connector assembly 4 can be removed from the empty device 1 and can be snapped with its arms 5 onto the neck portion of the cartridge body 2 of the cartridge to be filled. Subsequently, the connector assembly 4 together with the cartridge held between its arms 5 can be inserted into the receiving opening 23 of the device 1, where at the end of the insertion movement can be connected with the housing 18 by hooks which can be released with a release button (not shown) after the filling operation for removal of the filled cartridge. For insertion of the cartridge into the device, the slider assembly 6 with its pincer 7 can be positioned in the fully retracted position and the pincer 7 can be closed, i.e. the pincer arms 11a, 11b can be pushed towards each other by the rocker frame 9. While the cartridge can be inserted into the receiving opening 23 of the device 1, the free ends of the pincer arms 11a, 11b can be introduced into the central opening at the backside of the piston 3.

After the insertion movement has been completed, the motor 8 can be activated for turning the cam wheel 10 in a first rotational direction into a rotational position in which the protrusion 15 can no be longer supporting the end of the rocker frame 9 so that the pincer 7 can open and the pincer arms 11a, 11b can engage with their protrusions 12 the radial undercut formed by the ring 20 fixed in the central opening in the backside of the piston 3.

For filling the cartridge within the device 1 with insulin from an insulin reservoir (not shown), the cartridge can be connected, via a cannula (not shown) extending through the connector assembly 4 and a septum arranged at the head of the cartridge, to the insulin reservoir in such a manner that the inside of the insulin reservoir and the inside of the cartridge can communicate with each other while they can be hermetically sealed against the outside.

After the connection with the insulin reservoir has been established, the motor 8 can be activated for turning the cam wheel 10 further in the first rotational direction for moving the piston 3 forwards inside the cartridge body 2, thereby reducing the volume of the inside of the cartridge and thus displacing air from the inside of the cartridge into the insulin reservoir. When the pin 21 of the slider 6, during rotation of the cam wheel in the first rotational direction, reaches the end of the groove 14 in the cam wheel 10, the rotation of the cam wheel 10 can stop and the controller (not shown) of the motor 8 can detect an increasing electrical current consumption of the motor 8 indicating that the fully extended position of the piston 3 has been reached.

Now the controller of the motor 8 can reverse the rotational direction so that the cam wheel 10 can be rotated in a second rotational direction which can be opposite to the first rotational direction, thereby increasing the volume of the inside of the cartridge and thus displacing insulin from the inside of the insulin reservoir into the inside of the cartridge.

Alternatively, the forward movement of the piston can be performed before connecting the cartridge to the insulin reservoir so that there is no displacement of air into the insulin reservoir.

When the pin 21 of the slider 6, during rotation of the cam wheel in the second rotational direction, reaches the opposite end of the groove 14 in the cam wheel 10, the rotation of the cam wheel 10 can stop and the controller of the motor 8 can detect an increasing electrical current consumption of the motor 8 indicating that the fully retracted position of the piston 3 has been reached. Subsequently, the controller can shut off the motor 8.

Before the pin 21 reaches, when rotating the cam wheel in the second rotational direction, the end of the groove 14, the protrusion 15 can lift the end of the rocker frame 9, thereby automatically releasing the connection between the piston 3 and the slider assembly 6 by closing the pincer 7. To ensure that the piston 3 is released in the fully retracted position, the cam wheel can be designed in such a manner that, when the protrusion 15 starts lifting the end of the rocker frame 9, the piston 3 can have already reached the fully retracted position.

To remove the filled cartridge from the device 1, the release button for releasing the hooks which can connect the connector assembly 4 with the housing 18 can be pressed and the connector assembly 4 together with the cartridge can be removed from the device 1. Subsequently, the arms 5 of the connector assembly 4 can be unlatched and the filled cartridge can be separated from the connector assembly 4. The cartridge can then be ready for its intended use.

FIGS. 8a-g schematically illustrate the coupling and decoupling procedure of an alternative coupling concept that can also be used in the device. In this embodiment, a piston rod 6, i.e., the second portion, can be coupled to the piston 3 of the cartridge for moving it forwards and backwards inside the cartridge body 2. The piston rod 6 at its front end can comprise a lever arrangement 7, i.e., the second coupler, formed of two moveable levers 17a, 17b, i.e., the moveable parts, which at their free end carry protrusion 12.

As can be seen in FIG. 8a-c, the levers 17a, 17b can be held by leave springs 19 in a position that can introduce their free ends with the protrusions 12 into the central opening at the backside of the piston 3.

As can be seen 8d, the levers 17a, 17b can be designed in such a manner that, when for coupling the piston rod 6 to the piston 3 of the cartridge the piston rod 6 can be moved forward towards the piston 3 and can displace the piston 3 forwards inside the cartridge body 2, and thus the free ends of the levers 17a, 17b can be introduced into the central opening at the backside of the piston 3, the levers 17a, 17b can be tilted against the forces of the springs 19 through a contact with the backside of the piston 3 in such a manner that their protrusions 12 can engage a radial undercut 13 in the central opening in the backside of the piston. By this, a positive connection in both directions of the longitudinal axis of the cartridge body 2 between the piston 3 and the piston rod 6 can be established.

When now, as seen in FIG. 8d-g, during a subsequent backward displacement of the piston 3 inside the cartridge body 2 effected by a retracting movement of the piston rod 6, the piston 3 can reach a specific retracted position within the cartridge body 2, the levers 17a, 17b can be tilted, driven by the forces of the springs 19, back into their initial position, thereby removing the protrusions 12 from the radial undercut 13 in the central opening in the backside of the piston 3 so that, when the piston rod 6 is further retracted, it can separate from the piston 3 without pulling the piston 3 out of the cartridge body 2.

In another embodiment, the device can be a liquid pump, such as an insulin pump and the first coupler for holding the cartridge can be a cartridge compartment of the pump. In such an alternative embodiment, a plunger rod having the second coupler can be utilized and can provide the advantage of preventing the plunger of the cartridge from being drawn into the cartridge by a pressure differential (such as due to a height or ambient pressure difference). In this way, a pump incorporating the disclosed second coupler can exhibit the advantage of serving to prevent free-flow of a liquid (such as a liquid insulin solution) into a person using the pump.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for moving a piston inside a cartridge having a cartridge body and a piston arranged therein displaceable along a longitudinal axis of the cartridge body, the device comprising:
   a first portion having first coupler for releasably coupling the cartridge body of the cartridge to the first portion in such a manner that in both directions of the longitudinal axis of the cartridge body, a positive and/or frictional connection between the cartridge body and the first portion exists; and
   a second portion having second coupler for releasably coupling the piston of the cartridge to the second portion in such a manner that in both directions of the longitudinal axis of the cartridge body, a positive and/or frictional connection between the piston and the second portion exists;
   wherein the first and second portions move relative to each other in order to effect at least a forward displacement of the piston coupled to the second portion inside the cartridge body coupled to the first portion along the longitudinal axis of the cartridge body, and
   wherein the second coupler establishes and releases the positive and/or frictional connection with the piston and its shape is reversibly changed, the second coupler comprising a pincer having at least two pincer arms, the shape of which can be changed through a closing and opening movement of the pincer arms, and wherein the pincer arms comprise protrusions extending from them for engagement into radial undercuts formed in the piston of the cartridge to be filled;
   a drive; and
   a cam wheel rotated by the drive;
   wherein the pincer is guided in guides for linear movement and can be moved forwards and backwards by the cam wheel rotated by the drive, the pincer being coupled with the cam wheel via a pin or key formed at the pincer, which travels in a groove formed in a lateral surface of the cam wheel, and
   wherein the pincer can be opened and closed by a controller contacting contact surfaces of the pincer arms and moving relative to these contact surfaces of the pincer arms in direction of the longitudinal axis of the cartridge body to open or to close the pincer, the controller being operated by the cam wheel, and comprising a rocker frame that is pushed up by a protrusion formed at the cam wheel, thereby pushing together the arms of the pincer.

2. The device according to claim 1, further comprising, wherein the first and second portions move relative to each other in order to effect, a forward and backward displacement of the piston coupled to the second portion inside the cartridge body coupled to the first portion along the longitudinal axis of the cartridge body for use in filling the cartridge with a liquid.

3. The device according to claim 1, wherein the shape of the second coupler is at least partially affected through contact with the piston and/or with the cartridge body.

4. The device according to claim 1, wherein the shape of the second coupler is at least partially affected through a controller.

5. The device according to claim 1, wherein the shape of the second coupler is changed when the first and the second portions assume a specific position relative to each other.

6. The device according to claim 1, wherein the shape of the second coupler is automatically changed when the first and the second portions move into a specific position relative to each other and/or out of a specific position relative to each other.

7. The device according to claim 1, wherein the shape of the second coupler is changed into a coupled status when the cartridge body has been coupled to the first portion by the first coupler and/or that the shape of the second coupler is automatically changed when, after the cartridge body has been coupled to the first portion by the first coupler, the first coupler is released.

8. The device according to claim 1, wherein the second portion moves relative to the first portion forward and backward between a fully retracted position and a fully extended position along the longitudinal axis in order to effect, a forward and backward displacement of the piston inside the cartridge body, and the shape of the second coupler is automatically changed when the second portion is moved into the fully retracted position and/or is moved out of the fully retracted position.

9. The device according to claim 8, wherein the shape of the second coupler is automatically changed when starting from the fully retracted position, a forward movement of the second portion is initiated.

10. The device according to claim 1, wherein while the pincer is opened and closed by the controller operated by the cam wheel, the pincer is held by the cam wheel in a fully retracted position.

11. The device according to claim 1, wherein a rotationally flexible coupling is arranged between the drive and the cam wheel.

12. The device according to claim 1, wherein the device is a device for filling a cartridge with a liquid from a liquid reservoir, for dispensing a liquid from a cartridge containing a liquid, for dosing a liquid from a cartridge containing a liquid, or combinations thereof.

* * * * *